United States Patent [19]

Lee et al.

[11] Patent Number: 5,532,374

[45] Date of Patent: Jul. 2, 1996

[54] METHOD OF PREPARATION OF BIS-QUINOLINES

[75] Inventors: Virgil J. Lee, La Verne; Ying Wang, Diamond Bar; Carmen Taran, Glendora; Matthew L. Marocco, III, Santa Ana, all of Calif.

[73] Assignee: Hitachi Chemical Company, Ltd., Tokyo, Japan

[21] Appl. No.: 467,462

[22] Filed: Jun. 6, 1995

[51] Int. Cl.$^6$ .................................................. C07D 401/04
[52] U.S. Cl. ............................................................ 546/167
[58] Field of Search .............................................. 546/167

[56] References Cited

U.S. PATENT DOCUMENTS 4,400,499  8/1983  Colon ........................................ 528/174

OTHER PUBLICATIONS

Colon et al., "High Molecular Weight Aromatic Polymers by Nickel Coupling of Aryl Polychlorides," *J. Polym. Sci., Part A; Polym. Chem.*, 1990, vol. 28, pp. 367–383.
J. K. Stille, "Polyquinolines," *Macromolecules* 1981, vol. 14, pp. 870–880.

*Primary Examiner*—David B. Springer
*Attorney, Agent, or Firm*—Antonelli, Terry, Stout & Kraus

[57] ABSTRACT

Methods are provided for preparing bis-quinoline compounds, which include the steps of (1) condensing an aromatic 2-amino carbonyl compound and a methylene ketone compound to form an intermediate comprising a substituted quinoline having one chloro, one bromo, or one iodo substituent, followed by (2) reductive coupling of the quinoline, without its prior isolation or purification, using a transition metal catalyst, to thereby form the bis-quinoline compound.

10 Claims, No Drawings

METHOD OF PREPARATION OF BIS-QUINOLINES

FIELD OF THE INVENTION

This invention relates to new methods for preparing bis-quinoline compounds by (1) condensing an aromatic 2-amino carbonyl compound and a methylene ketone compound to form an intermediate comprising a substituted quinoline having one chloro, one bromo, or one iodo substituent, followed by (2) reductive coupling of the quinoline, without its prior isolation or purification, using a transition metal catalyst, to thereby form the bis-quinoline compound.

BACKGROUND OF THE INVENTION

Bis-quinoline compounds can be used, inter alia, as fluorescent dyes or as monomers for the preparation of polyquinolines.

In known processes for preparing bis-quinolines, including bis-quinoline monomers, an intermediate is prepared which is then isolated from the reaction mixture and purified. The purified intermediate is then further processed to provide the bis-quinoline.

The isolation and purification of the intermediate requires the use of manpower, equipment, and time which increases the production cost. In addition, such isolation and purification results in waste streams, e.g., which result from treatment or disposal of recrystallization solvents. Finally, isolation and purification of intermediates results in losses and hence reduced product yields.

There is, therefore, a need in the art for a process where a bis-quinoline can be formed via an intermediate, where the intermediate need not be isolated and purified prior to being further processed to the final bis-quinoline material.

SUMMARY OF THE INVENTION

The present invention provides an economical method for forming bis-quinoline compounds. The method includes the steps of condensing an aromatic 2-amino carbonyl compound and a methylene ketone to form a substituted quinoline intermediate having one chloro, bromo, or iodo substituent. Without isolating or purifying the intermediate, the quinoline intermediate is reductively coupled using a transition metal catalyst to thereby form the bis-quinoline.

DETAILED DESCRIPTION

This invention provides an efficient and economical method for forming various bis-quinoline compounds via an aryl halide intermediate, where the intermediate need not be isolated from the reaction mixture and purified prior to being reacted to form the final bis-quinoline product. More particularly, the method of the present invention involves a Friedlander condensation reaction between 2-amino aromatic aldehydes or ketones (hereinafter also referred to as o-amino carbonyl compounds) bearing halide substituents, where the halide substituent is chloride, bromide, or iodide, preferably chloride, and ketones with at least one α-methyl or α-methylene unit (α-methylene ketones), followed by a transition metal catalyzed aryl halide coupling reaction. As is described below in detail, depending on the specific coupling reaction used, nickel or copper are the preferred transition metal catalyst systems. Surprisingly, the transition metal coupling can be carried out in the same vessel as an acid catalyzed Friedlander condensation even though transition metal catalyzed coupling reactions are known to be sensitive to acids. For example, we have found that simple neutralization of the Friedlander acid catalyst with base results in good yields of bis-quinoline compounds via the nickel catalyzed couplings without isolation of the intermediates.

The bis-quinolines provided in accordance with practice of the present invention are useful, inter alia, as fluorescent dyes or as monomers for the preparation of polyquinolines.

In one exemplary embodiment of practice of the present invention, the method provides a more facile and less costly route to prepare 6,6'-bis[2-(4-fluorophenyl)- 4-phenylquinoline] (Compound 1) from 4'-fluoroacetophenone (Compound 2) and 2-amino-5-chlorobenzophenone (Compound 3) via the intermediate 6-chloro-2-(4-fluorophenyl)-4-phenylquinoline (Compound 4) as shown in the Scheme 1 reaction sequence below. The Compound 4 (aryl halide) intermediate is not isolated or purified during the synthesis.

Scheme 1

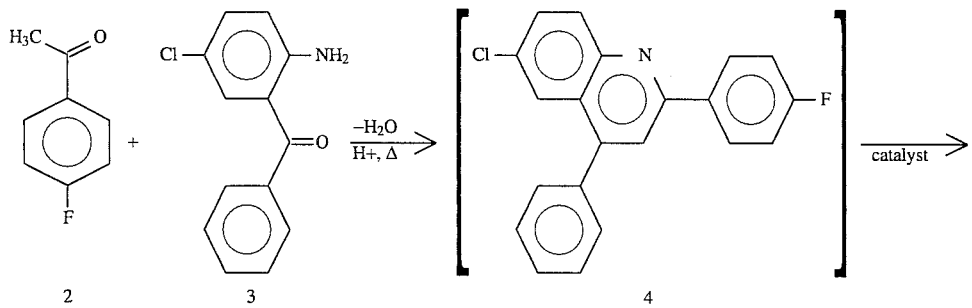

-continued
Scheme 1

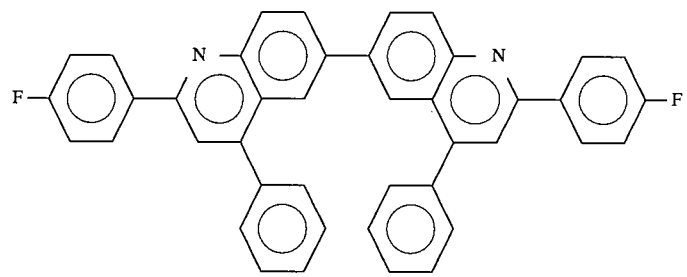

1

Scheme 1

In another embodiment, the aryl halide intermediate is coupled in an anhydrous aprotic solvent with a catalyst mixture comprising a nickel compound or complex, a phosphite ligand, and a reducing metal to thereby provide the bis-quinoline compound.

In general terms, the process of the present invention includes the Friedlander condensation to form an aryl halide intermediate, which is then coupled in the presence of a transition metal catalyst system. In a preferred embodiment of the present invention, the transition metal coupling reaction is performed in the same flask, tank, reactor, or other vessel, as that used for the Friedlander reaction.

In a preferred embodiment, the general procedure for preparing the bis-quinolines of the present invention comprises the steps of (1) allowing an α-methylene ketone to react with an o-aminoaryl carbonyl, with or without an inert solvent, in the presence of an acid or base condensation catalyst; (2) adding of a base to neutralize any acid catalyst used; (3) removing the water of condensation by heating and evacuating, distillation, or by addition of a solvent which forms an azeotrope with water followed by azeotropic distillation; (4) if necessary, changing the solvent to one suitable for nickel catalyzed coupling; (5) adding a nickel coupling catalyst, including a nickel salt or complex, a ligand, an optional promoter, and a reducing agent selected from the group consisting of aluminum, magnesium, manganese, and zinc; (6) raising the temperature to about 60° C. to 100° C. for about 30 minutes to 12 hours; and (7) recovering the product.

Steps 1–6 may all be carried out without changing the reaction vessel. Step 1 is a Friedlander condensation usually carried out at a temperature of about 100° C. to 200° C., with continuous removal of water of condensation. Useful solvents for the Friedlander condensation include, but are not limited to, benzene, cresol, toluene, tetrahydrofuran, and the like. It is preferable to use no solvent for the Friedlander condensation step. Suitable acid catalysts for the Friedlander condensation can be either protonic or Lewis acids and include para-toluenesulfonic acid (tosic acid), methanesulfonic acid, sulfuric acid, phosphoric acid, polyphosphoric acid, trifluoroacetic acid, HF, HCl, HBr, HI, boron trifluoride, aluminum chloride, and the like. Suitable base catalysts for the Friedlander condensation include alkali and alkali earth hydroxides, N-ethyl morpholine, triethyl amine, 1,5-diazabicycloo[4.3.0]non-5-ene, 1,4-diazabicyclo[2.2.2]octane, and the like. Friedlander condensations are well known in the art, and have been used, for example, to prepare polyquinoline polymers as disclosed in U.S. Pat. No. 4,000,187 issued Dec. 28, 1976, and J. K. Stille, "Polyquinolines," *Macromolecules,* 1981, 14, pp. 870–880, both of which are incorporated herein by reference.

In Step 2, any acid remaining from the Friedlander condensation is neutralized. Bases suitable for neutralization in Step 2 are alkali and alkaline earth bicarbonates, carbonates, and hydroxide. Suitable solvents for azeotropic distillation used in step 3 are benzene and toluene. Chlorinated solvents, such as chlorobenzene, should be avoided to prevent interference in the nickel coupling step. Solvents such as benzene, and toluene which are inert to nickel coupling are preferred, since they may be left in the reaction mixture after azeotropic distillation. Any transition metal coupling catalyst system may be used in Step 5.

Where the halide group on the quinoline intermediate is bromo or iodo, copper catalyzed Ullman coupling may be used. Ullman coupling of aryl halides, which uses copper as the transition metal, is well known in the art, and appropriate conditions will be apparent to one skilled in the art. See for example, P. E. Fanta, "The Ullman Synthesis of Biaryls," *Synthesis,* 9, 9–21, 1974. Where the halide group on the quinoline intermediate is chloro or bromo, nickel catalyzed coupling is preferred. Non-limiting examples of effective nickel coupling catalyst mixtures include the nickel halide/triphenylphosphine/reducing metal catalyst system disclosed by Colon et al in U.S. Pat. Nos. 4,326,989 and 4,400,499 and the nickel halide/bidentate phosphine/reducing metal catalyst system disclosed by Puckett in U.S. Pat. No. 4,939,309. U.S. Pat. Nos. 4,326,989, 4,400,499, and 4,939,309 are incorporated herein by this reference. Additionally, nickel halide/phosphite catalyst systems, described below in detail, can be used for the aryl halide coupling.

The nickel salt or complex catalyst used in the coupling may be any nickel salt or coordination compound that will coordinate phosphine or phosphite ligands, including but not limited to, nickel(II)chloride, nickel (II)bromide, nickel (II)acetate, nickel (I)chloride, nickel (I)bromide, nickel (II) sulfate, nickel (0)bis-cyclooctadiene, nickel (II) bis-triphenylphosphine dichloride, nickel(II)tris-2,2'-bipyridine, and the like. Nickel salts of oxidizing anions, such as nitrate, and perchlorate should not be used as these anions will react with the reducing metal. Hydrated nickel complexes may be used if the water of hydration is removed, for example, by azeotropic distillation before addition of the reducing metal. Where arylphosphines are used as the ligand, non-limiting examples of such arylphosphines include triphenylphosphine, tri-2-tolylphosphine, tri-4-tolylphosphine, 1,4-bis-diphenylphosphinobutane, tri-4-methoxyphenylphosphine, and the like. Triphenylphosphine is the preferred phosphine as it is lowest in cost.

The reducing metal used in the coupling reaction is preferably zinc, more preferably zinc dust, and most preferably activated zinc dust (e.g. activated by washing with HCl in diethyl ether, followed by washing with diethyl ether and drying). In the Ullman and Colon catalyst systems, the relative amounts of ligand, reducing agents, and promoter are well-known in the art, while the molar ratio of aryl halide substrate to nickel catalyst should be about 10:1 to about 1000:1, preferably about 20:1 to 100:1, and most preferably about 50:1. In the nickel phosphite catalyst system, the ratio of phosphite ligand to nickel should be from about 2:1 to about 10:1, preferably in the range of from about 2.4:1 to 5:1, more preferably in the range of from about 2.5:1 to 3.5:1, and most preferably in the range of from about 2.8:1 to 3.2:1. The amount of promoter may range from 0.01M to 1M, preferably from 0.1 to 0.5M, and most preferably from 0.2M to 0.4M. The ratio of reducing metal to aryl halide should be from about 2:1 to 1:1 on an equivalent basis, preferably about 1.1:1. The molar ratio of aryl halide to nickel catalyst should be from about 2:1 to 10,000:1, preferably from about 10:1 to 1,000:1, and most preferably from about 50:1 to 100:1.

The method of product recovery in Step 7 is not critical, and any method known in the art is suitable. For highly aromatic products that are soluble in hot NMP, but poorly soluble in cold NMP, the reaction mixture may be heated to about 160° C. to fully dissolve the product, filtered hot to remove unreacted reducing metal, cooled to let the product crystallize, and filtered to recover product.

In one preferred embodiment, phosphites useful in conducting the aryl halide coupling reaction have the general structural formula:

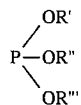

wherein R', R', and R'" are independently selected from the group consisting of $C_3$ to $C_{22}$ alkyl, $C_6$ to $C_{24}$ aryl, alkaryl, and aralkyl.

In the definition of $C_6$–$C_{24}$ aryl groups, the number of carbons (C) refers to the carbons in the ring structure itself. For example,

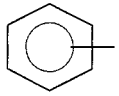 is a $C_6$ aryl;

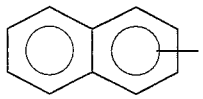 is a $C_{10}$ aryl; and

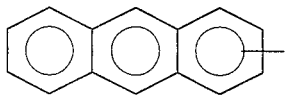 is a $C_{14}$ aryl.

Examples of phosphite ligands useful to couple the intermediates include the following:

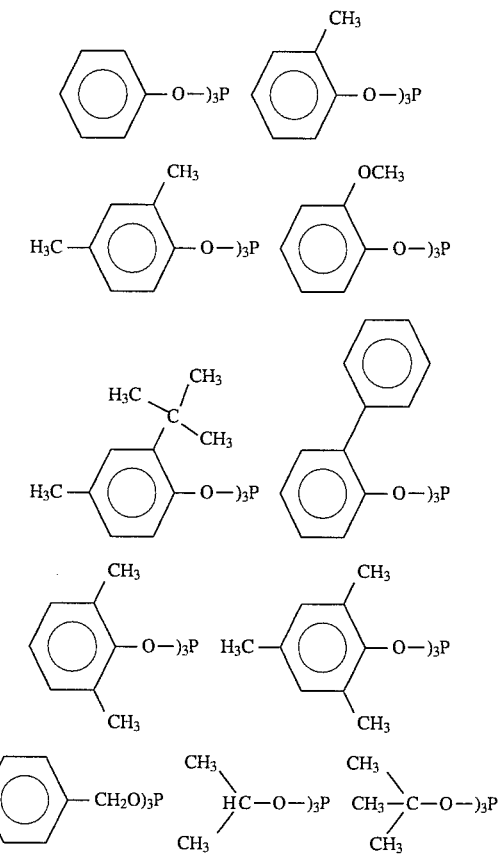

Additional non-limiting examples of phosphite groups include diphenylisopropylphosphite, di-o-tolylnaphthylphosphite, tert-butyl-4-fluorophenylphenylphosphite. Tri-2-tolylphosphite is preferred because of its relatively low cost, and because it is of appropriate size to produce an active nickel phosphite catalyst.

A preferred embodiment of the process of the present invention for condensing an aromatic 2-amino carbonyl compound and a α-methylene ketone compound to form an aryl halide intermediate and then reductive coupling of the intermediate to prepare a bis-quinoline in the absence of isolating and purifying the aryl halide intermediate, is set forth below (the aryl halide intermediate is not shown):

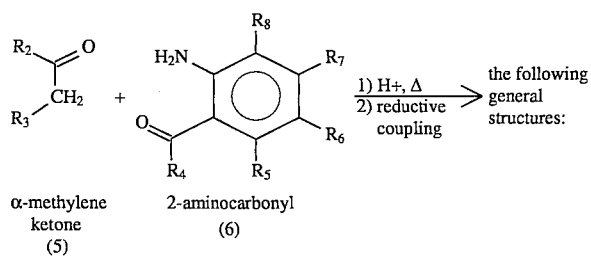

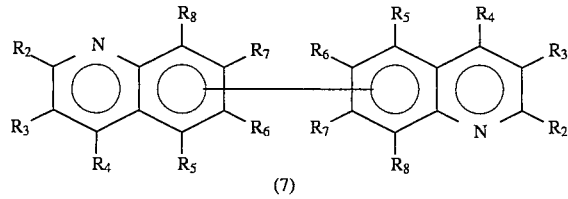

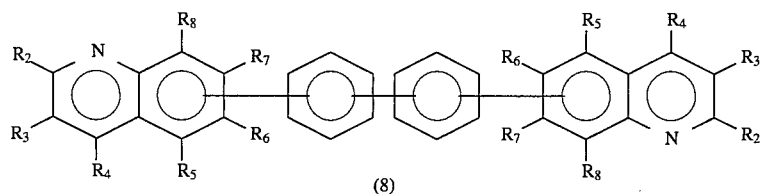

where the linkage between the quinoline nuclei is symmetrical and may be at any position $R_2$–$R_8$. The linkage may be either direct as in formula (7) or via a biphenyl group as in formula (8), wherein $R_2$, $R_3$, and $R_4$ are independently selected from the group consisting of H, alkyl, aryl, fluoroalkyl, fluoroaryl, chloroaryl, bromoaryl, and iodoaryl; $R_5$, $R_6$, $R_7$, and $R_8$ are independently selected from the group consisting of H, alkyl, aryl, fluoroalkyl, alkoxy, aryloxy, fluoroalkoxy, alkylthio, arylthio, cyano, fluoro, chloro, bromo, iodo, fluoroaryl, chloroaryl, bromoaryl, and iodoaryl; and one and only one of $R_2$, $R_3$, $R_4$, $R_5$, $R_6$, $R_7$, and $R_8$ contains a chloride, bromide or iodide. The intermediate has exactly one chloride, bromide, or iodide which will react with the coupling catalyst in the next step and dictates the position of coupling to give product dimer.

The $R_2$–$R_8$ alkyl and fluoroalkyl groups are $C_1$–$C_{22}$ alkyl, and the aryl, fluoroaryl, chloroaryl, bromoaryl, and iodoaryl are $C_6$–$C_{24}$ aryl.

General structure (8) may have the biphenyl linking group at any of seven possible positions on the quinoline nuclei. Three more particular structures of general structure (8) are:

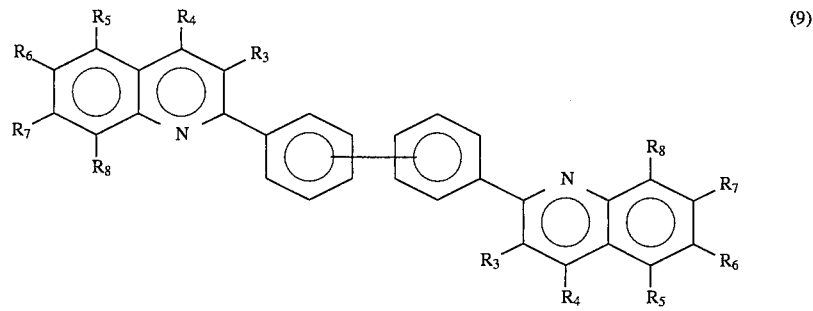

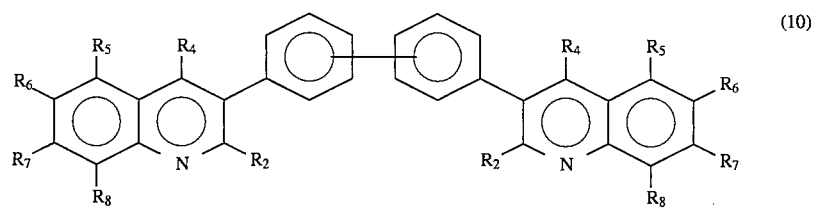

-continued

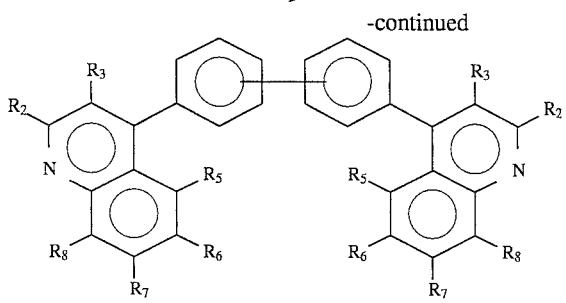

(11)

Additional groups may be present on any of the R groups as long as they do not interfere with either the Friedlander condensation or the nickel coupling reaction. Such groups include, but are not limited to, alkyl, aryl, fluoroalkyl, fluoroaryl, heteroaryl, alkoxy, aryloxy, fluoro, alkylthio, arylthio, and cyano. Non-limiting examples of G-methylene ketones (5) useful in practice of the present invention include cetophenone, 2'-fluoroacetophenone, 4'-fluoroacetophenone, 2'-chloroacetophenone, 3'-chloroacetophenone, 4'-chloroacetophenone, 4'-bromoacetophenone, propiophenone, 2'-, 3'-, and 4'-chloropropiophenone, 2'-, 3'-, and 4'-fluoropropiophenone, 2-phenylacetophenone (deoxybenzoin), 2-phenyl-2'-chloroacetophenone, 2-phenyl-3'-chloroacetophenone, 2-phenyl-4'-chloroacetophenone, 2-(2-fluorophenyl)acetophenone, 2-(3-fluorophenyl)acetophenone, 2-(4-fluorophenyl)acetophenone, 2-(2,4-fluorophenyl)acetophenone, 2'-chloro-2-(2-fluorophenyl)acetophenone, 2'-chloro-2-(3-fluorophenyl)acetophenone, 2'-chloro-2-(4-fluorophenyl)acetophenone, 4'-chloro-2-(2-fluorophenyl)acetophenone, 4'-chloro-2-(3-fluorophenyl)acetophenone, 4'-chloro-2-(4-fluorophenyl)acetophenone, 2-(2-chlorophenyl)-2'-fluoroacetophenone, 2-(3-chlorophenyl)-2'-fluoroacetophenone, 2-(4-chlorophenyl)-2'-fluoroacetophenone, 2-(2-chlorophenyl)-4'-fluoroacetophenone, 2-(3-chlorophenyl)- 4'-fluoroacetophenone, 2-(4-chlorophenyl)- 4'-fluoroacetophenone, 4'-chloro-2-(4-phenoxyphenyl)acetophenone, 4'-fluoro-2-(4-phenoxyphenyl)acetophenone, and 2-(4-fluoro-2-phenoxyphenyl)acetophenone.

Non-limiting examples of o-aminocarbonyl compounds (6) useful in practice of the present invention include 2-aminobenzophenone, 2-amino-3-chlorobenzophenone, 2-amino-4-chlorobenzophenone, 2-amino-5-chlorobenzophenone, 2-amino-6-chlorobenzophenone, 2-amino-2'-chlorobenzophenone, 2-amino-3'-chlorobenzophenone, 2-amino-4'-chlorobenzophenone, 2-amino-3-fluorobenzophenone, 2-amino-4-fluorobenzophenone, 2-amino-5-fluorobenzophenone, 2-amino-6-fluorobenzophenone, 2-amino-2'-fluorobenzophenone, 2-amino-3'-fluorobenzophenone, 2-amino-4-fluorobenzophenone, 2-amino-3-chloro-4'-fluorobenzophenone, 2-amino-4-chloro-2'-fluorobenzophenone, 2-amino-5-chloro-4'-fluorobenzophenone, 2-amino-6-chloro-4'-fluorobenzophenone, 2-amino-2'-chloro-6-fluorobenzophenone, 2-amino-3'-chloro-4-fluorobenzophenone, 2-amino-4'-chloro-6-fluorobenzophenone, 2-amino-4-chloro-3-fluorobenzophenone, 2-amino-4'-chloro-4-fluorobenzophenone, 2-amino-4'-chloro-5-fluorobenzophenone, 2-amino-3'-chloro-6-fluorobenzophenone, 2-amino-4,4'-difluorobenzophenone, 2-amino-4-chloro-3'-fluorobenzophenone, 2-amino-4-chloro-4'-fluorobenzophenone, 2-aminobenzaldehyde, 2-amino-3-chlorobenzaldehyde, 2-amino-4-chlorobenzaldehyde, 2-amino-5-chlorobenzaldehyde, 2-amino-6-chlorobenzaldehyde, 2-amino-2'-chlorobenzaldehyde, 2-amino-3'-chlorobenzaldehyde, 2-amino-4'-chlorobenzaldehyde, 2-amino-3-fluorobenzaldehyde, 2-amino-4-fluorobenzaldehyde, 2-amino-5-fluorobenzaldehyde, 2-amino-6-fluorobenzaldehyde, 2-amino-2'-fluorobenzaldehyde, 2-amino-3'-fluorobenzaldehyde, and 2-amino-4'-fluorobenzaldehyde.

The α-methylene ketones and o-aminocarbonyl compounds used as starting materials in practice of the present invention are either available commercially or can be readily synthesized by a person of skill in the art.

Non-limiting examples of aryl halide intermediates contemplated to be formed in practice of the present invention include 2-(2-chlorophenyl)quinoline, 2-(3-chlorophenyl)quinoline, 2-(4-chlorophenyl)quinoline, 2-(2-chlorophenyl)- 4-phenylquinoline, 2-(3-chlorophenyl)-4-phenylquinoline, 2-(4-chlorophenyl)-4-phenylquinoline, 2-(4-chlorophenyl)-3,4-diphenylquinoline, 6-chloro-4-phenylquinoline, 6-chloro-3,4-diphenylquinoline, 6-chloro-2,4-diphenylquinoline, 6-chloro-2,3,4-triphenylquinoline, 5-chloro-2-phenylquinoline, 2-(4-chlorophenyl)-3-(4-fluorophenyl)quinoline, 3-(4-chlorophenyl)-2-(4-fluorophenyl)quinoline, 2-(4-chlorophenyl)-3-(4-fluorophenyl)-4-phenylquinoline, 3-(4-chlorophenyl)-2-(4-fluorophenyl)-4-phenylquinoline, 2-(3-chloro-4-fluorophenyl)quinoline, 6-chloro-2-(2-fluorophenyl)-4-phenylquinoline, 6-chloro-2-(4-fluorophenyl)-4-phenylquinoline, 6-chloro-4-(2-fluorophenyl)-2-phenylquinoline, 6-chloro-4-(4-fluorophenyl)-2-phenylquinoline, 6-chloro-3-(4-fluorophenyl)-4-phenylquinoline, 6-chloro-3-(2-fluorophenyl)-2-phenylquinoline, 6-chloro-3-(4-fluorophenyl)-2-phenylquinoline, 6-chloro-3,4-diphenyl-2-(4-fluorophenyl)quinoline, 6-chloro-3,4-diphenyl-2-(2-fluorophenyl) quinoline, 2-(2-chlorophenyl)fluoroquinoline, 2-(3-chlorophenyl)-6-fluoroquinoline, (4-chlorophenyl)-6-fluoroquinoline, 2-(2-chlorophenyl)-fluoro- 4-phenylquinoline, 2-(3-chlorophenyl)-6-fluorophenylquinoline, 2-(4-chlorophenyl)-6-fluorophenylquinoline, 3-(2-chlorophenyl)-6-fluorophenylquinoline, 3-(3-chlorophenyl)-6-fluorophenylquinoline, 3-(4-chlorophenyl)-6-fluorophenylquinoline, 6-chloro-2-(pentafluorophenyl)-4-phenylquinoline, 6-chloro-2-(4-fluorophenyl)-3-methyl-4-phenylquinoline, 2-(4-chlorophenyl)-3-(4-fluorophenyl)-4-phenylquinoline, 3-(4-chlorophenyl)-2-(4-fluorophenyl)-4-phenylquinoline, and 2-(4-chlorophenyl)-7-fluoro-4-(4-fluorophenyl)quinoline.

The Friedlander step in the process of the present invention is catalyzed by acids or bases, such as those identified above, and is performed either neat (without added solvent) or in a solvent or solvent mixture that is useful for the nickel coupling reaction. Non-limiting examples of effective solvents include N,N-dimethylacetamide, N-methylpyrrolidone, N-cyclohexylpyrrolidone, and N,N-dimethylformamide.

As is known in the art the nickel/ligand/zinc catalyst systems used for aryl halide coupling require anhydrous conditions. Any water or other source of protons including acids, and protic solvents such as alcohols, will lead to reductive replacement of the chloro, bromo or iodo group with hydrogen instead of the desired coupling to a biaryl. It was therefore surprising that an acid catalyzed Friedlander reaction could be followed by a nickel coupling reaction without rigorous purification of the intermediate. We have found that neutralization of any acid present following a Friedlander reaction followed by careful drying is sufficient for the nickel coupling step. Drying may be by any method known in the art, including but not limited to, azeotropic distillation, as for example with a Dean-Stark trap or other apparatus for separating the water/organic distillate, drying with molecular sieves or other absorbent, either batchwise or with a column, drying with a chemical drying agent such as magnesium sulfate, and the like. Drying by azeotropic distillation is a preferred method.

Although the entire process including the Friedlander reaction, neutralization, drying, and nickel catalyzed coupling may be carried out without removing the reactants from the original reactor, it may be convenient to transfer the reactants to a different reactor because of timing, scheduling, storage, maintenance or other factors. In this case the intermediate may be moved, pumped or transferred to a different vessel, but it need not be purified further than as specified above.

Some illustrative examples of bis-quinolines prepared in accordance with practice of the present invention, in no way intended to limit the scope of the invention, are as follows:

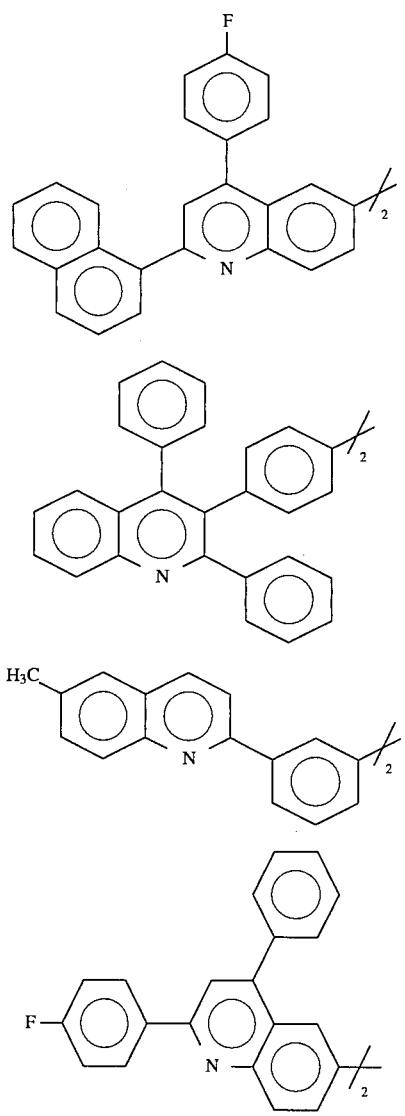

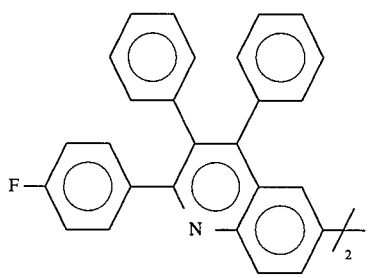

The following examples are illustrative of the present invention but is not considered limiting thereof in any way.

EXAMPLE 1

Preparation of Activated Zinc Dust

Activated zinc dust is obtained after 2 washings of commercially available 325 mesh zinc dust with 1M hydrogen chloride in diethyl ether (anhydrous) followed by washings with diethyl ether (anhydrous) and drying in vacuo or under inert atmosphere for several hours at about 100°–200° C. If clumps form during drying the zinc dust is re-sieved to −150 mesh. This material should be used immediately or stored under an inert atmosphere away from oxygen and moisture.

EXAMPLE 2

Preparation of 6,6'-bis[2-(4-fluorophenyl)-4-phenylquinoline]

(Compound 1)

A 250 mL, three-necked, round-bottomed flask fitted with a mechanical stirring set-up, a short path distillation apparatus, and a nitrogen inlet valve was charged with 2-amino-5-chlorobenzophenone (Compound 3) (17.4 g, 75.0 mmol), 4'-fluoroacetophenone (Compound 2) (10.0 mL, 824 mmol), and tosic acid (0.505 g, 2.7 mmol). The reaction was heated under nitrogen at 180° C. (20 h) to effect condensation and water removal. The temperature of the reaction was lowered to 160° C., and potassium carbonate (0.367 g, 2.7 mmol) was added. Toluene (100 mL) was then added to the reaction and distilled away. This toluene addition/distillation was repeated two times.

The temperature of the reaction was lowered to 80° C., and the distillation unit was removed. The flask was charged with nickel chloride (0.778 g, 6.00 mmol), sodium iodide (2.43 g, 16.2 mmol), tris(2-tolyl)phosphite (6.77 g, 19.2 mmol), and NMP (63 mL), and the resulting solution was stirred (18 h). The reaction temperature was then lowered to 60° C., and activated zinc dust (6.59 g, 101 mmol) was added. After the exotherm had subsided (10 min), the reaction was allowed to stir at 80° C. (16 h).

The temperature of the reaction was raised to 160° C. to dissolve the precipitate which had formed. The reaction mixture was filtered while hot through Celite and was allowed to cool to room temperature. The crude product was collected by filtration and was washed with ethanol. A second crop was collected from the mother liquor and was washed with ethanol. The yellow product was dried in a vacuum oven at 160° C. (18 h). 12.0 g from Crop 1 and 6.3 g from Crop 2 (Yield 73.1%).

EXAMPLE 3

Preparation of
6,6'-bis[2-(4-fluorophenyl)-phenylquinoline]

(Compound 1)

A 250 mL, three-necked, round-bottomed flask fitted with a nitrogen inlet, a stirring rod set up, and a distillation unit was charged with 2-amino-5-chlorobenzophenone (17.38 g, 75.0 mmol), 4'-fluoroacetophenone (10.0 mL, 82.0mmol), and p-tosic acid (1.00 g, 5.3 mmol). The reaction was heated to 180° C. under nitrogen (16 h) and water removed by distillation. To the reaction was added 0.726 g $K_2CO_3$ and toluene (2×50 mL) was successively added to the reaction mixture and removed through the distillation set up to assure removal of the last traces of water.

The reaction was cooled to room temperature and a mixture containing bis(triphenylphosphine)nickel dichloride (0.681 g, 1.04 mmol), sodium iodide (1.40 g, 9.37 mmol), triphenylphosphine (8.19 g, 33.3 mmol), and activated zinc dust (3.13 g, 47.9 mmol) were added to the reaction flask along with NMP (86 mL). The flask was heated under nitrogen to 70° C. (16 h). The mixture was diluted with NMP (10 mL), the temperature was raised to 170° C., and the mixture was filtered through Celite. The mother liquor was cooled to −20° C. and the product was collected by filtration. The yellow solid was washed with cold ethanol/methylene chloride (3/1) and was dried in a vacuum oven at 100° C. Yield 18.03 g, 80.5%.

The above descriptions of various embodiments of processes for preparing bis-quinolines are for illustrative purposes. Because of variations which will be apparent to those skilled in the art, the present invention is not intended to be limited to the particular embodiments described above. Additionally, it should be understood that any compounds or compositions that are not described in the application as being useful for practicing the invention are not needed and the invention can be practiced in their absence. The scope of the invention is defined in the following claims.

What is claimed is:

1. A method for forming a bis-quinoline, the method comprising the steps of:

condensing an aromatic 2-amino carbonyl compound and a methylene ketone compound to form a substituted quinoline intermediate having one substituent selected from the group consisting of chloro, bromo, and iodo; and, without isolating or purifying the substituted quinoline intermediate, reductive coupling said quinoline intermediate using a transition metal catalyst to thereby form the bis-quinoline.

2. The method of claim 1, wherein the aromatic 2-amino carbonyl is 2-amino-5-chlorobenzophenone.

3. The method of claim 1, wherein the methylene ketone is 4'-fluoroacetophenone.

4. The method of claim 1, wherein the catalyst is a nickel triarylphosphine complex.

5. The method of claim 1, wherein the catalyst is a nickel phosphite catalyst.

6. The method of claim 1, wherein the substituted quinoline intermediate has one chloro substituent.

7. The method according to claim 6, wherein the substituted quinoline comprises at least one fluoro substituent.

8. The method of claim 1, wherein the methylene ketone has the structure:

and the 2-amino carbonyl has the structure:

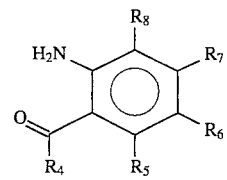

wherein $R_2$, $R_3$, and $R_4$ are independently selected from the group consisting of H, $C_1$–$C_{22}$ alkyl, $C_6$–$C_{24}$ aryl, fluoroalkyl, fluoroaryl, chloroaryl, bromoaryl, and iodoaryl; $R_5$, $R_6$, $R_7$, and $R_8$ are independently selected from the group consisting of H, $C_1$–$C_{22}$ alkyl, $C_6$–$C_{24}$ aryl, fluoroalkyl, alkoxy, aryloxy, fluoroalkoxy, alkylthio, arylthio, cyano, fluoro, chloro, bromo, iodo, fluoroaryl, chloroaryl, bromoaryl, and iodoaryl; and the groups $R_2$, $R_3$, $R_4$, $R_5$, $R_6$, $R_7$, and $R_8$ taken together contain only one chloride, bromide or iodide substituent.

9. The method according to claim 8, wherein at least one of the $R_2$–$R_8$ groups contains a fluoro substituent.

10. The method according to claim 8, wherein the catalyst is a nickel phosphite catalyst.

* * * * *